US009366241B2

(12) United States Patent
Tschanz

(10) Patent No.: US 9,366,241 B2
(45) Date of Patent: Jun. 14, 2016

(54) PLUNGER PUMP FOR VOLUMES BELOW ONE MICROLITER, ALLOWING MANUAL INTERVENTION

(75) Inventor: Peter Tschanz, Gerlikon (CH)

(73) Assignee: MMI AG, Glattbrugg (CH)

( * ) Notice: Subject to any disclaimer, the term of this patent is extended or adjusted under 35 U.S.C. 154(b) by 202 days.

(21) Appl. No.: 13/641,256

(22) PCT Filed: Apr. 12, 2011

(86) PCT No.: PCT/EP2011/055698
§ 371 (c)(1),
(2), (4) Date: Nov. 21, 2012

(87) PCT Pub. No.: WO2011/141253
PCT Pub. Date: Nov. 17, 2011

(65) Prior Publication Data
US 2013/0064693 A1    Mar. 14, 2013

(30) Foreign Application Priority Data

Apr. 15, 2010    (EP) ..................................... 10160010

(51) Int. Cl.
*F04B 19/00*    (2006.01)
*F04B 9/02*    (2006.01)
(Continued)

(52) U.S. Cl.
CPC .......... *F04B 19/006* (2013.01); *A61M 5/31578* (2013.01); *A61M 5/31583* (2013.01); *F04B 9/02* (2013.01); *H02K 7/06* (2013.01)

(58) Field of Classification Search
CPC .......... F04B 19/006; F04B 17/03; F04B 9/02; B01F 15/0462; B01L 3/0227; H02K 7/06; H02K 5/00; B05C 17/0103; B05C 17/0133; A61M 5/31578; A61M 5/31583
USPC .......... 417/415; 604/131, 155; 310/12.31, 90, 310/91, 80, 12.14, 12.19, 20, 15; 222/325, 222/333, 326, 386, 390
See application file for complete search history.

(56) References Cited

U.S. PATENT DOCUMENTS 3,390,815 A * 7/1968 Kavan .................. B01L 3/0206
222/137
3,415,419 A * 12/1968 Jewett et al. .................. 222/333
(Continued)

FOREIGN PATENT DOCUMENTS

DE       2442622 B1 * 3/1976 .............. F16H 25/20
JP    20062881178        10/2006
(Continued)

OTHER PUBLICATIONS

Hamilton Company Syringes (https://web.archive.org/web/20070621170817/http://www.hamiltoncompany.com/syringes/microliter.asp, archived data from Jun. 21, 2007).*

*Primary Examiner* — Devon Kramer
*Assistant Examiner* — Nathan Zollinger
(74) *Attorney, Agent, or Firm* — Pabst Patent Group LLP

(57) ABSTRACT

An automated high-precision plunger pump for volumes of less than 1 microliter, which is used in the microscope-assisted micromanipulation of biological material, comprises a housing (1) and a pump head (8) that defines a working chamber (9) with a common or separate inlet and outlet opening (10), wherein the volume of the working chamber (9) can be altered by an axially movable plunger (7) that can be introduced into it. The plunger (7) is axially movable via a threaded spindle (5) or a spindle nut (6) arranged in threaded engagement on the threaded spindle (5), and the threaded spindle (5) and/or the spindle nut (6) can be rotationally driven and the respective other component is designed to be rotationally lockable.

6 Claims, 1 Drawing Sheet

(51) Int. Cl.
*A61M 5/315* (2006.01)
*H02K 7/06* (2006.01)

(56) References Cited

U.S. PATENT DOCUMENTS

| | | | |
|---|---|---|---|
| 3,631,847 A * | 1/1972 | Hobbs, II | 600/432 |
| 4,406,158 A * | 9/1983 | Allington | 73/61.57 |
| 4,465,475 A * | 8/1984 | Mardorf | A61M 5/1456 128/DIG. 1 |
| 5,219,099 A * | 6/1993 | Spence et al. | 222/325 |
| 5,244,461 A | 9/1993 | Derlien | |
| 5,545,140 A | 8/1996 | Conero | |
| 5,738,728 A * | 4/1998 | Tisone | 118/638 |
| 6,475,188 B1 * | 11/2002 | Baxter | 604/131 |
| 6,610,030 B1 | 8/2003 | Baxter | |
| RE38,281 E * | 10/2003 | Tisone | 422/521 |
| 7,080,936 B1 * | 7/2006 | Simpson | 366/162.3 |
| 7,193,521 B2 * | 3/2007 | Moberg et al. | 340/679 |
| 2002/0022802 A1 | 2/2002 | Simpson | |
| 2003/0086213 A1 | 5/2003 | Shin | |
| 2010/0001814 A1 | 1/2010 | Lobl | |

FOREIGN PATENT DOCUMENTS

| | | |
|---|---|---|
| JP | 2007330572 | 12/2007 |
| WO | 9010468 | 9/1990 |
| WO | 0025844 | 5/2000 |

* cited by examiner

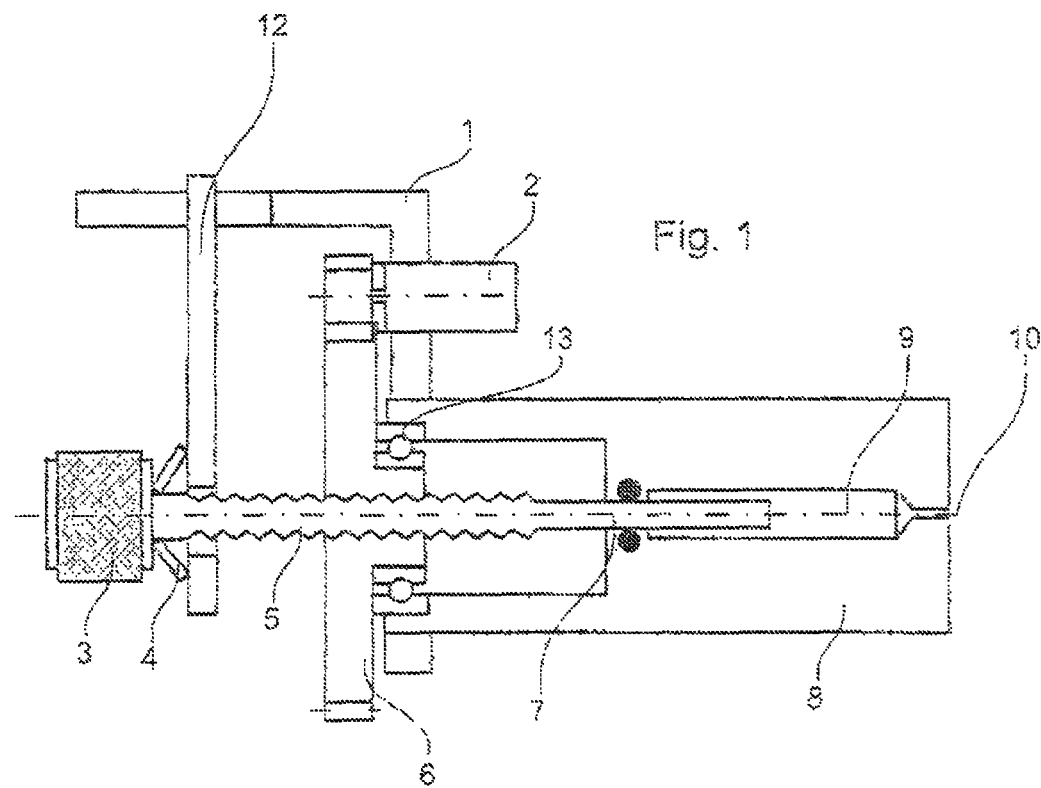
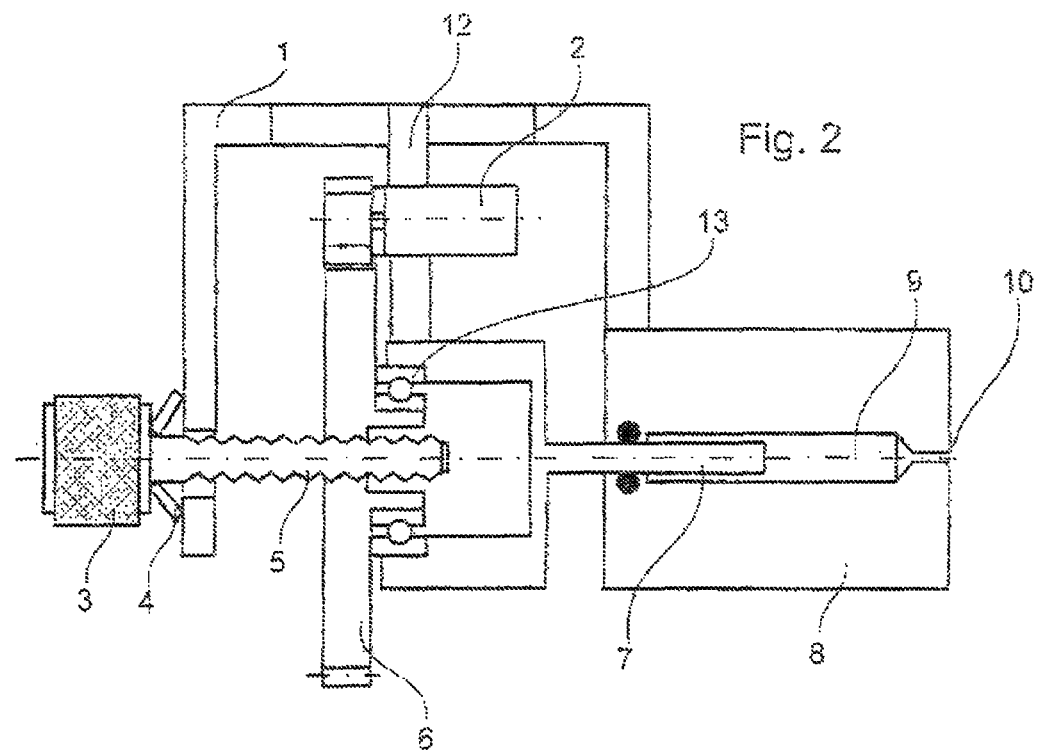

PLUNGER PUMP FOR VOLUMES BELOW ONE MICROLITER, ALLOWING MANUAL INTERVENTION

CROSS REFERENCE TO RELATED APPLICATIONS

This application is a national phase filing under 35 U.S.C. §371 of PCT/EP2011/055698 filed under the Patent Cooperation Treaty on Apr. 12, 2011, which claims priority to and benefit of foreign application EP 10160010.4, filed on Apr. 15, 2010, the contents of each being hereby incorporated by reference in their entirety.

The present invention relates to a high-precision plunger pump with the possibility of manual intervention, for volumes of less than 1 microliter according to the preamble of claim 1.

PRIOR ART

The molecular analysis of pure enriched cell cultures or even individual cells is an important prerequisite of medical genomics and proteomics, and could become extremely important in the future for a medical profiling of patients. Hitherto this objective could be achieved only with difficulty and took a not inconsiderable amount of time on account of mechanical and also process technology restrictions in the cell manipulation (e.g. the collection of cells or microinjection). In particular the isolation of individual as well as unusual cells from minute samples necessary for the genotype and phenotype characterization proved to be very difficult, since individual cells had to be detected under a microscope by research staff and the detected cells then had to be manipulated manually with the aid of capillaries. For this purpose it is necessary to move an accurately defined fluid volume in the capillaries, for example in order to extract individual cells or cell contents via the capillary, or to inject constituents of other cells (for example cell nuclei) into a cell, without thereby damaging the cell by too much aspirated or injected material.

One of the limitations mentioned above concerns in particular the pumps used for the volume measurement and provision of the low pressure/excess pressure, which must be capable of aspirating and expelling very precisely fluid volumes of the order of magnitude of less than 1 microliter down to 1 nanoliter. Since on account of the small pump volumes and the therefore small pump dimensions, the necessary hermeticity of the pump piston with respect to the pump cylinder in piston pumps can be achieved only with great difficulty, so-called plunger pumps are employed in the manipulation of cell material, in which the plunger has to be sealed only at the point in which it passes into the cylinder.

In order to maintain the aforedescribed volumetric precision with simultaneous coordination with the cell detection under the microscope, the detection and also manipulation of the cells is furthermore carried out partly manually, for example with the CellTram microinjectors of the Eppendorf company or the XenoWorks™ microinjectors of the Butter Instrument company, in which the plunger is actuated by turning a handwheel. Such a manual procedure in the cell manipulation is of course extremely time intensive and is therefore becoming increasingly less suitable for the constantly increasing number of samples to be processed, not least on account of the necessary labor costs.

On the other hand it is known to operate the aforementioned manual pumps via a drive motor coupled to the handwheel. A further attempt at automation of the manipulation system was undertaken with the Nanojet 11 microinjection pipettes of the Drummond Science company, in which the plunger is coupled directly to a microprocessor-controlled electric motor. With the aforementioned motorized pumps there is however the problem that their drives are very slow and therefore service interventions, such as for example the "backfilling" with fluid necessary with each change of capillary, are very time-consuming or even impossible. Also, it is not possible to operate the motorized pumps for this purpose in a simple way by hand, since in the case of the motorized handpump the motor first of all has to be decoupled, which is complicated, while with the automated microinjection pipette a manual actuation is not envisaged at all.

DESCRIPTION OF THE INVENTION

The object of the present invention is accordingly to provide an automated plunger pump for volumes of less than 1 microliter, which can be operated automatically as well as manually, allows the possibility of manual intervention for filling and maintenance, and is not mechanically sensitive while having a high volumetric precision. This object is achieved with the aid of an automated high-precision plunger pump that has the features defined in claim 1. Further advantageous embodiments are disclosed in the subclaims.

The automated high-precision plunger pump according to the invention comprises a housing and a pump head, which defines a working chamber with a common or separate inlet and outlet opening, wherein the volume of the working chamber can be changed by an axially movable plunger that can be introduced therein and the plunger is axially movable by means of a threaded spindle or a spindle nut threadedly engaged on the threaded spindle, and the threaded spindle and/or the spindle nut are designed so that they can be rotatably driven and rotatably locked.

By virtue of this construction the plunger pump according to the invention has two drive trains that can be mechanically decoupled from one another, since the axial movement of the plunger can be effected either by driving the threaded spindle or by driving the spindle nut, independently of in each case the other drive train. In order to move the plunger for example to fill the pump, it is therefore no longer necessary, as in the prior art, to decouple one drive train, which is complicated, and on account of the direct coupling of the drive on the threaded nut a pump that is simple to operate can be provided that is just as precise for service or maintenance purposes. Such service and maintenance interventions are in this connection not restricted only to the filling of pump medium, but include inter alia also the rinsing or cleaning of the working chamber and the capillary/pipette that can be connected thereto. These interventions are therefore activities that have to be carried out relatively frequently, which now takes substantially less time thanks to the quicker and simpler operation of the pump.

Overall the invention therefore provides a plunger pump that with low mechanical effort provides a fast, efficient and thus cheaper micromanipulation of biological material, which is characterized by reliability and safety of the mechanical parts, and which has an excellent user friendliness, since the user has the possibility of intervening in the process of cell collection.

Preferably the plunger pump comprises as drive means a motor, which is engaged with the spindle nut and/or the threaded spindle and via which it is operatively connected to the rotationally lockable threaded spindle or the rotationally lockable spindle nut for driving the plungers. If for example the spindle nut, which is rotatably incorporated in the housing, is driven by the motor, then the rotationally locked threaded spindle, which is in threaded engagement with the spindle nut, moves in the axial direction, whereby also the plunger connected to the threaded spindle is moved and the volume of the working chamber of the pump changes.

In a preferred configuration the threaded spindle and/or the spindle nut are provided with an upstream gear mechanism. In this way it is possible to adapt the axial displacement of the plunger in an optimum manner to the preferred rotational speed of the motor and to alter it as a function of the latter. On the other hand such a gear mechanism (for example a planetary gear) can allow a manual intervention in a simple manner, in other words can provide intervention points for a mechanical rotation of the gear mechanism, which is then converted into a movement of the plunger. As a further option the threaded spindle actuated in the hand drive could also be motorized with a corresponding conversion.

In a particularly preferred embodiment of the plunger pump the lockable threaded spindle, the lockable spindle nut or the motor is provided with a coupling, which advantageously is a slip clutch. This coupling is therefore a safety feature and prevents mechanical damage to the sensitive drive train and motor of the pump should the pump be subjected to excess loads, for example by penetration of a foreign body into the working chamber or by incorrect use on the part of the user. The coupling can in this connection be manual but however can also be automated.

The plunger is preferably co-rotatingly connected to the threaded spindle, which is a type of connection that can be realized easily and inexpensively. This can for example be achieved by a (releasable) frictional grip between the plunger and threaded spindle. In particular in this connection the plunger can also be connected to the threaded spindle in a torsionally rigid manner, which has the advantage that the plunger does not rotate in the necessary seal and therefore wear and tear of the seal is reduced.

In a further advantageous embodiment of the plunger pump the pump head is provided with preferably direction-oriented valves leading into the working chamber. This additionally facilitates the replenishment of the pump medium, and the direction orientation, for example in the form of a non-return valve, prevents an undesirable outflow of the pump medium.

Finally, it is advantageous to provide limit switches in the pump head, which specify the end positions of the plunger in the working chamber. These limit switches can be connected to a control, which ensures that the plunger does not impact against the axial end wall of the working chamber, and that the threaded spindle or the spindle nut do not become displaced or turned beyond their end positions.

BRIEF DESCRIPTION OF THE DRAWINGS

FIG. 1 is a schematic sectional view of a first embodiment of the automated high-precision plunger pump according to the invention, and FIG. 2 is a schematic sectional view of a second embodiment of the automated high-precision plunger pump according to the invention.

WAYS OF IMPLEMENTING THE INVENTION

Preferred embodiments of the present invention are described hereinafter with reference to the drawings. To start with, for a better understanding of the field of use of the invention the automated isolation of arbitrary individual or unusual cells is described, which takes place in three steps: cell recognition, cells collection and cell release.

The inventors have for this purpose developed a system that is based on an inverse microscope (reverse microscope), a cell recognition unit, an automated capillary adjustment, an automated pump and a sliding table. The collection and release are controlled by means of a high-precision pump (described in detail hereinafter), which enables process procedures to be defined that employ nanoliter volumes of a pump medium for the cell separation process and thus provide the basis for a molecular analysis of the cell material to be carried out at the end of the process in just 1 microliter of medium.

The (non-adhering) cells thus do not experience any kind of mechanical stresses: the cell collection takes place simply on account of the liquid flow surrounding the cell. Under optimal conditions even partially adhering cells can be collected in this way. There is no contact between the cells and the capillary used for the collection. The capillary diameter can be significantly larger than that of the cell. For example, cells of 6 µm diameter can be collected efficiently with a capillary of 40 µm diameter.

The cells can be released on various cell carriers (deposits). So-called "grid deposits" are in this connection either grid-like point deposits (such as for example AmpliGrid®) or small vessels arranged in a grid-like manner (such as the IBIDI sample pocket slides). Individual point deposits can consist of a transparent cover, a PCR test tube or a microfluid device. However the target carrier is formed, its size should in general not exceed the size of standard slides, so that these can be used in the multiple slide holder on the sliding table.

The collection and release of the cells can take place in various ways, ranging from the manual to the fully automated mode of operation with cell recognition. However, even with the manual operating mode it is not necessary to operate any components of the system (microscope, pump, capillary) by hand: all operating procedures are started by the user from a PC.

The essential mode of operation of the plunger pump for the collection and release of the cells is now described with the aid of FIG. 1, which shows a schematic sectional view of a first embodiment of the plunger pump according to the invention. The plunger pump comprises a housing 1 and a pump head 8 firmly fixed on the housing. The pump head 8 includes a working chamber 9, which in operation contains the pump medium, for example an oil or an inert fluid for the biological material to be collected. It is however also conceivable to use air or a gas as pump medium. The working chamber is in the present embodiment formed elongated and similar to a syringe, and has at one end an inlet and outlet opening, through which the pump medium is aspirated or expelled.

A plunger (plunger piston) 7 is introduced via a seal at the other end of the elongated working chamber 9, which plunger can move axially in the working chamber (i.e. along the longitudinal extension of the working chamber) and due to its own volume displaces the corresponding volume of the fluid contained in the working chamber. In other words, the available volume of the working chamber can be altered by moving the plunger 7 backwards and forwards. At its end facing away from the working chamber the plunger 7 is connected to a threaded spindle 5, this connection being shown as a rigid connection in FIG. 1, although it can also be formed so as to freely rotate about a bearing.

The threaded spindle 5, which is mounted in an axially movable holder 12 in the housing, is likewise displacably arranged relative to the housing and engages via its thread with a spindle nut 6, which is non-displacably but rotatably mounted in the housing 1 (or in the pump head 8). The spindle nut 6 is in turn in threaded engagement with the shaft of an electric motor 2 and is rotatably driven by this. In addition a handwheel 3 for the manual operation of the pump is provided on the end of the threaded spindle 5 remote from the plunger 7.

A slip clutch 4, which for example through the spring force of a shaft shoulder counteracts and in normal operation prevents a rotation of the handwheel 3 and thus a rotation of the threaded spindle 5, is disposed between the handwheel 3 and the holder 12.

In operation the spindle nut 6 is therefore caused to rotate by the electric motor 2, this rotation of the non-displacable spindle nut 6 being converted into a longitudinal movement of the non-rotating (locked) threaded spindle 5, which in turn displaces the plunger 7 of the pump axially in the working chamber. Due to the direct drive of the threaded nut 6 a very accurate and controllable displacement of the plunger 7 can thus be obtained, which corresponds to a very accurately defined change of volume in the nanoliter range. With this very accurate change in volume an exactly defined flow of pump medium can in turn be generated, by means of which individual cells or cell constituents can be separated and collected.

Should it be necessary in operation to correct the fluid flow or the pump volume or replenish the pump medium, then the plunger pump can be actuated via the handwheel 3. For this, first of all the motor 2 and the rotation of the spindle nut 6 are stopped. By turning the handwheel 3 the locking action of the slip clutch 4 is overcome and the threaded spindle 5 is rotated in the housing. Since the motor 2 is switched off and the spindle nut 6 does not rotate (is locked), the threaded spindle 5 turns through the nut 6 and moves the plunger 7 in the axial direction in the working chamber 9.

A second embodiment of the plunger pump according to the invention is illustrated in FIG. 2. In contrast to the first embodiment of FIG. 1, in this case the threaded spindle 5 is not coupled directly, i.e. in a translational manner, to the plunger 7. Instead the plunger 7 is connected via a roller bearing to the spindle nut 6, which together with its drive motor 2 is axially movably arranged in the housing 1, i.e. is not fixed to the housing 1, and can thus be axially displaced together with the plunger. The threaded spindle 5 on the other hand is mounted in a translationally fixed manner on the housing 1 and is rotationally fixed via a friction clutch. When the motor 2 is in operation the spindle nut 6 rotates and thus moves axially on the threaded spindle 5 rotationally fixed by the friction clutch. In this way the spindle nut 6 also moves the plunger 7 in the axial direction in the working chamber 9.

Should an excessive torque act on the threaded spindle 5 in the case of the plunger pumps of the two embodiments described in FIGS. 1 and 2, then the slip clutch 4 slips and allows the rotation of the threaded spindle 5, so that the translational movement of the spindle nut 6 is stopped. In this way it is ensured that the sensitive mechanics of the plunger pump are not damaged on account of operational errors or other circumstances.

The invention claimed is:

1. An automated high-precision plunger pump for volumes of less than 1 microliter, comprising
    a housing, a motor, a handwheel, a clutch, and a pump head and two drive trains comprising a threaded spindle and spindle nut,
    the pump head comprising a working chamber with a common or separate inlet and outlet opening,
    the plunger pump comprising a movable plunger configured to be introduced axially into the working chamber so as to alter the volume thereof,
    wherein the threaded spindle and spindle nut are arranged in threaded engagement,
    wherein the plunger is axially movable by the threaded spindle or the spindle nut,
    wherein the threaded spindle nut is configured to be rotationally lockable with the aid of the clutch,
    wherein the spindle nut is engagement with the motor and is rotationally driven by it, and wherein the handwheel is provided at the end of the threaded spindle remote from the plunger to manually drive the plunger pump,
    wherein the threaded spindle can be mechanically decoupled from the spindle nut,
    wherein the threaded spindle can rotate independent of the spindle nut and the spindle nut can rotate independent of the threaded spindle,
    wherein the clutch in normal operation prevents a rotation of the handwheel and the threaded spindle, and
    wherein either the plunger is co-rotatingly connected in a torsionally rigid manner to the threaded spindle or the plunger is connected to the spindle nut via a roller bearing.

2. The plunger pump according to claim 1, wherein the threaded spindle and/or the spindle nut are provided with an upstream gear mechanism.

3. The plunger pump according to claim 1 wherein the clutch is a slip clutch, wherein the clutch is manual or automated.

4. The plunger pump according to claim 1, wherein the pump head is provided with one or more direction-oriented valves leading into the working chamber.

5. The plunger pump according to claim 1, further comprising one or more limit switches in the pump head, wherein the one or more limit switches specify the end positions of the plunger in the working chamber.

6. An automated high-precision plunger pump for volumes of less than 1 microliter, comprising
    a housing, a motor, a clutch, a pump head and two drive trains comprising a threaded spindle and a spindle nut,
    the pump head comprising a working chamber with a common or separate inlet and outlet opening,
    the plunger pump comprising a movable plunger configured to be introduced axially into the working chamber so as to alter the volume thereof,
    wherein the threaded spindle and spindle nut are arranged in threaded engagement,
    wherein the plunger is axially movable by either the threaded spindle or the spindle nut,
    wherein one of the threaded spindle and the spindle nut is configured to be rotationally lockable with the aid of the clutch which prevents mechanical damage to the sensitive drive train and the motor of the pump should the pump be subjected to excess loads,
    wherein the spindle nut is in engagement with the motor and is rotationally driven by it,
    wherein one of the threaded spindle or spindle nut is provided with an upstream gear mechanism providing intervention points allowing a manual intervention for a mechanical rotation of the gear mechanism, which is then converted into a movement of the plunger, wherein the drive trains can be mechanically decoupled from one another, and
    wherein either the plunger is co-rotatingly connected in a torsionally rigid manner to the threaded spindle or the plunger is connected to the spindle nut via a roller bearing.

* * * * *